US011213273B2

(12) United States Patent
Cathier et al.

(10) Patent No.: US 11,213,273 B2
(45) Date of Patent: Jan. 4, 2022

(54) INTEGRATION OF ULTRASOUND AND X-RAY MODALITIES

(71) Applicant: KONINKLIJKE PHILIPS N.V., Eindhoven (NL)

(72) Inventors: Pascal Yves François Cathier, Asnières-sur-Seine (FR); Olivier Pierre Nempont, Suresnes (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 321 days.

(21) Appl. No.: 16/398,462

(22) Filed: Apr. 30, 2019

(65) Prior Publication Data

US 2019/0254623 A1 Aug. 22, 2019

Related U.S. Application Data

(63) Continuation of application No. 14/442,427, filed as application No. PCT/IB2013/060582 on Dec. 3, 2013, now abandoned.

(30) Foreign Application Priority Data

Dec. 3, 2012 (EP) .................................. 12306503

(51) Int. Cl.
*A61B 8/08* (2006.01)
*A61B 6/12* (2006.01)
(Continued)

(52) U.S. Cl.
CPC .............. *A61B 8/0841* (2013.01); *A61B 6/12* (2013.01); *A61B 6/4085* (2013.01); *A61B 6/4417* (2013.01); *A61B 6/4441* (2013.01); *A61B 6/461* (2013.01); *A61B 6/5247* (2013.01); *A61B 6/54* (2013.01); *A61B 8/0883* (2013.01); *A61B 8/12* (2013.01); *A61B 8/4416* (2013.01); *A61B 8/4483* (2013.01); *A61B 8/461* (2013.01); *A61B 8/5261* (2013.01); *A61B 8/54* (2013.01)

(58) Field of Classification Search
None
See application file for complete search history.

(56) References Cited

U.S. PATENT DOCUMENTS 6,529,766 B1 * 3/2003 Guendel ................. A61B 6/12
600/411
7,211,045 B2 5/2007 Dala-Krishna et al.
(Continued)

FOREIGN PATENT DOCUMENTS

CN 1476311 A 2/2004
CN 101283929 A 10/2008
(Continued)

*Primary Examiner* — Yi-Shan Yang

(57) ABSTRACT

A method for ultrasound image acquisition for tracking an object of interest in ultrasound image information includes receiving X-ray image information and ultrasound image information, determining, before the tracking, a spatial relationship between the X-ray image information and the ultrasound image information, detecting an object of interest in the X-ray image information and steering two-dimensional ultrasound image acquisition such that the object of interest is within an ultrasound image plane.

15 Claims, 3 Drawing Sheets

(51) Int. Cl.
  *A61B 6/00* (2006.01)
  *A61B 8/00* (2006.01)
  *A61B 8/12* (2006.01)

(56) References Cited

U.S. PATENT DOCUMENTS

| | | | |
|---|---|---|---|
| 7,314,446 B2 * | 1/2008 | Byrd | A61B 8/065 |
| | | | 600/443 |
| 8,131,041 B2 | 3/2012 | Mors et al. | |
| 8,792,964 B2 | 7/2014 | Maschke | |
| 9,468,413 B2 | 10/2016 | Hall et al. | |
| 10,238,361 B2 | 3/2019 | Gogin et al. | |
| 2002/0173719 A1 | 11/2002 | Zhao et al. | |
| 2003/0074011 A1 * | 4/2003 | Gilboa | A61B 5/06 |
| | | | 606/130 |
| 2007/0282221 A1 | 12/2007 | Wang et al. | |
| 2008/0146919 A1 | 6/2008 | Camus et al. | |
| 2008/0188749 A1 | 8/2008 | Rasche et al. | |
| 2008/0234570 A1 | 9/2008 | Olivier et al. | |
| 2009/0185657 A1 | 7/2009 | Klingenbeck-Regn | |
| 2010/0063400 A1 | 3/2010 | Hall et al. | |
| 2010/0166147 A1 | 7/2010 | Abenaim | |
| 2010/0298704 A1 | 11/2010 | Pelissier et al. | |
| 2011/0007139 A1 | 1/2011 | Brunetti | |
| 2012/0245458 A1 | 9/2012 | Gogin et al. | |
| 2012/0296202 A1 | 11/2012 | Mountney et al. | |
| 2013/0237814 A1 | 9/2013 | Marcovici | |
| 2017/0105685 A1 | 4/2017 | Schafer et al. | |

FOREIGN PATENT DOCUMENTS

| | | |
|---|---|---|
| DE | 4021102 A1 | 7/1990 |
| DE | 102007021061 A1 | 11/2008 |
| RU | 2378989 C2 | 1/2010 |
| WO | 2006109219 A1 | 10/2006 |
| WO | 2011070477 A1 | 6/2011 |
| WO | 20110114259 A1 | 9/2011 |
| WO | 2012067607 A1 | 5/2012 |

* cited by examiner

INTEGRATION OF ULTRASOUND AND X-RAY MODALITIES

CROSS-REFERENCE TO PRIOR APPLICATIONS

This application is a continuation of U.S. application Ser. No. 14/442,427, "Integration of Ultrasound and X-Ray Modalities." U.S. application Ser. No. 14/442,427 is a National Stage application under 35 U.S.C. § 371 of International Application Serial No. PCT/IB2013/060582, filed on Dec. 3, 2013, which claims the benefit of EP Application Serial No. 12306503.9, filed on Dec. 3, 2012. These applications are hereby incorporated by reference herein.

FIELD OF THE INVENTION

The present invention relates to image acquisition technology. In particular, the present invention relates to tracking of an object of interest in ultrasound image information. More particularly, the present invention relates to a method for ultrasound image acquisition, a system for ultrasound image acquisition, a computer-readable medium as well as a program element for ultrasound image acquisition.

BACKGROUND OF THE INVENTION

A current trend in interventional procedures is a tighter integration of ultrasound and X-ray modalities. In other words, different image modalities are not employed separately but rather conjointly during a specific procedure. Thereby, drawbacks of certain modalities may be compensated by advantages of other modalities.

E.g., although modern interventional ultrasound solutions offer the possibility of 3D imaging, it is often relied upon two-dimensional ultrasound imaging for various reasons. Amongst those reasons may be a higher image quality, a higher frame rate and no need for cropping, volume orientation or rendering parameter tuning when employing two-dimensional ultrasound images versus 3D imaging.

For interventional procedures, an object of interest, e.g. the tool by which the procedure is performed, is depicted in the image information acquired by the respective modalities. By depicting said object or overlaying image information of said object and the image information of a respective modality, a person performing the procedure readily obtains visual information about the location and/or orientation of the object of interest with regard to anatomic structures shown in the modality's image information. E.g., the path of a tool tip through tissue, may be tracked in the respective image information, i.e. visually followed by the person performing the procedure. Such tracking thus allows to reconfirm the correctness of a procedure, i.e. whether the procedure is correctly conducted.

However, during transcatheter intracardiac procedures, such as mitral clip or arterial fibrillation ablation, transcatheter tools being employed, e.g. a mitral clip or ablation catheter, are rather narrow objects that may experience substantive passive motion due to breathing, heartbeat and blood flow as well as active motion due to the interventionist steering the tool.

In such procedures, ultrasound images are regularly acquired by employing a transesophageal echocardiogram or TEE. The TEE is performed by a specialized probe being inserted into a patient's esophagus, which contains an ultrasound transducer at its tip. The ultrasound transducer is adapted for image acquisition and Doppler evaluation of ultrasound images. TEEs regularly provide clearer images, especially with regard to tissue structures that are difficult to view transthoracically, i.e. through the chest wall by employing an external ultrasound transducer.

Since the TEE itself lies in the esophagus, it experiences very low levels of motion. In particular for transcatheter procedures, the motion of the TEE probe regularly is below the motion of transcatheter tools previously described. In other words, the spatial relationship and/or the distance between the transcatheter tool and the TEE transducer is non-constant and consequently, when considering 2D image acquisition of a particular ultrasound plane, the tool tip periodically goes out of an ultrasound plane currently under observation.

To make the tool tip appear again in the imaging plane, readjustment of the imaging plane is required. This in turn requires a tedious coordination between the interventionist operating the transcatheter tool and the echographer operating in particular the ultrasound image acquisition device.

SUMMARY OF THE INVENTION

It is an object of the invention to allow steering of two-dimensional ultrasound image acquisition, in particular steering of an imaging plane of an ultrasound image acquisition device, so that an object of interest remains visible, in particular without continuous readjustment of imaging parameters.

Accordingly, a method for ultrasound image acquisition, in particular for tracking an object of interest in ultrasound image information, a system for ultrasound image acquisition, a computer-readable medium as well as a program element for ultrasound image acquisition according to the independent claims are provided. Preferred embodiments may be taken from the dependent claims.

These and other aspects of the present invention will become apparent from and elucidated with reference to the embodiments described hereinafter. Exemplary embodiments of the present invention will be described below with reference to the following drawings.

The illustration in the drawings is schematic. In different drawings, similar or identical elements are provided with similar or identical reference numerals.

The figures are not drawn to scale, however may depict qualitative proportions.

DETAILED DESCRIPTION OF EMBODIMENTS

Figure 1:
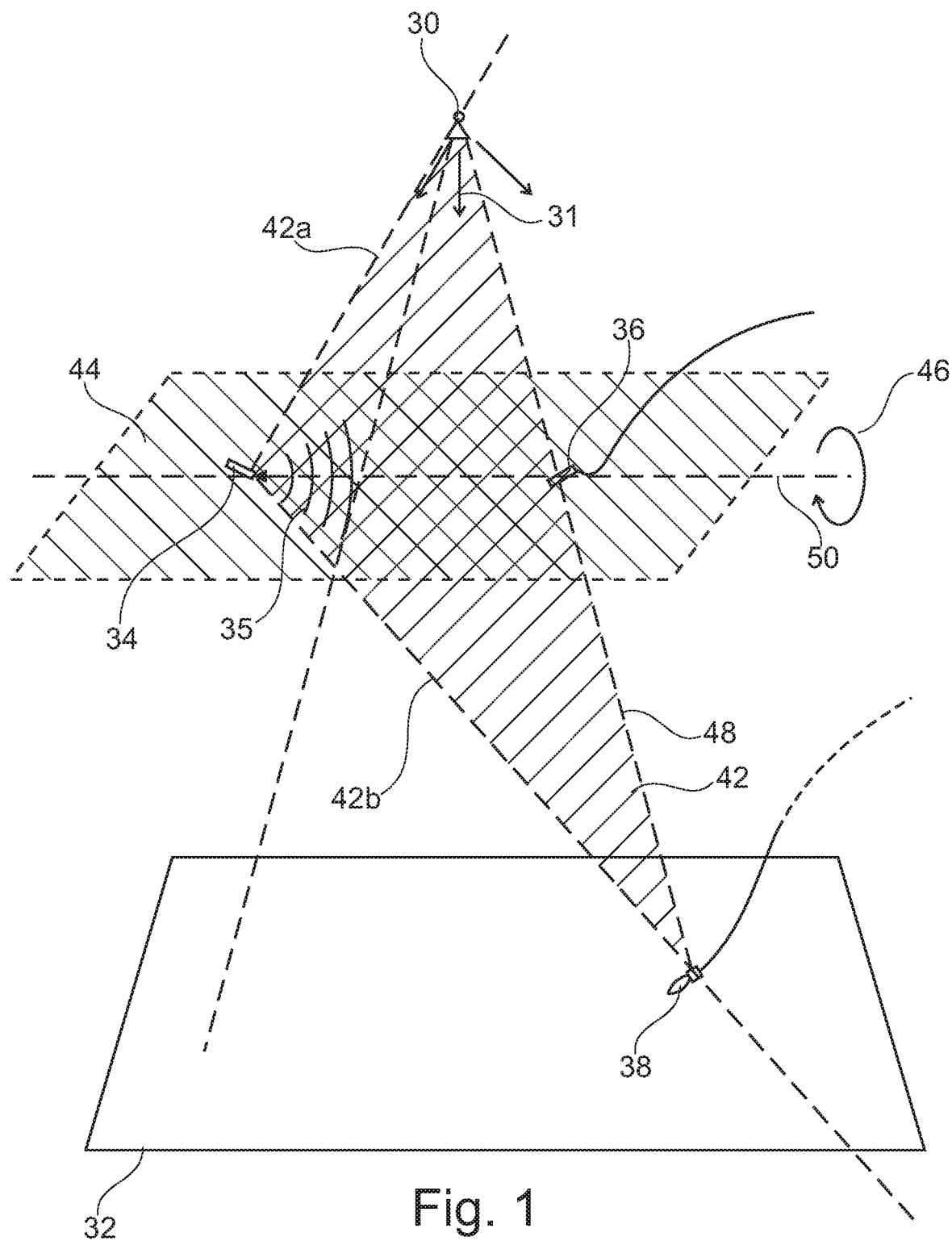
FIG. 1 shows an exemplary embodiment of the relationship between ultrasound image information and X-ray image information according to the present invention.

One aspect of the present invention pertains to steering and/or aligning an imaging plane of an ultrasound image so that an object of interest remains visible, i.e. within the imaging plane, without the requirement of, in particular constant, readjustment of imaging parameters, in particular ultrasound plane position and orientation.

During a certain interventional procedure, both an X-ray imaging modality e.g. by using a C-arc, as well as an ultrasound imaging modality like TEE may be employed, with each modality generating in particular two-dimensional image information.

Regularly, the ultrasound transducer comprises a transducer array for obtaining image information of a particular, two-dimensional ultrasound image plane, which can be adjusted in 3D by varying the ultrasound emissions of the transducer array.

One aspect of the present invention is that the orientation of an ultrasound plane is steered such that the ultrasound plane comprises the X-ray source. Further, in case the ultrasound imaging plane also contains the projection of an object of interest, e.g. a tool tip of a transcatheter tool, on the X-ray detector, said spatial information is sufficient to establish an ultrasound imaging plane, in which the tool tip of a transcatheter tool may move without being able to leave the ultrasound plane. In other words, in case the ultrasound plane is steered to (always) contain the X-ray source as well as the projection of the tool tip visible in the X-ray image information, which projection however is non-static on the X-ray detector and may thus move, thereby requiring adjustment of the imaging plane, the tool tip of the transcatheter tool will remain visible within the ultrasound plane. Thereby, the ultrasound plane is automatically steered such that the object of interest lies within the image. No additional use of three-dimensional images is required, which in this case would only be used for tracking the tool tip while degrading the frame rate of the ultrasound image acquisition.

The steering of the ultrasound plane according to the present invention allows to present a moving object of interest inside the ultrasound plane, thereby avoiding a repetitive appearance and disappearance of the object due to out of plane movement, either due to active motion of the object of interest or passive motion e.g. due to the cardiac beats.

To allow the implementation of the method for ultrasound image acquisition according to the present invention, it is first assumed that the ultrasound image information and X-ray image information are registered. In other words, the spatial relationship between the ultrasound image information and C-arm imaging information, in particular comprising further information such as the relative position of an X-ray source, is known. E.g., when considering a two-dimensional X-ray image as well as a two-dimensional ultrasound image, the angle and position of both images with respect to each other is assumed to be known in case said data is registered. Also, a common coordinate system or reference coordinate system may be established and subsequently employed, thereby spatially linking the C-arm imaging information and the ultrasound image information. Further, particular image information visible in either two-dimensional image is also assumed to be known. One example of registering ultrasound image information and X-ray image information is described in international patent application WO 2011/070477 of the instant applicant.

Further, it is assumed that the imaging plane of the ultrasound image information may be steered electronically, e.g. by employing a suitable ultrasound transducer array as known in the art.

Also, it is assumed that the object of interest can be tracked, i.e. is visual and detectable within the X-ray image information. In other words, the X-ray image shall contain a projection of the object of interest, e.g. the tool tip of the transcatheter tool.

Subsequently, the ultrasound plane is steered such that both the X-ray source as well as the tracked/projected object of interest in the X-ray image is contained in the ultrasound plane. In other words, the X-ray source as well as the tracked object of interest in the X-ray image describe two independent and precisely defined points of the ultrasound imaging plane. Since the ultrasound imaging plane also passes through the ultrasound probe or the ultrasound transducer, which therefore provides a third defined point, the ultrasound plane is completely and precisely determined. Since the ultrasound plane is thus readjusted continuously so that the X-ray source as well as the tracked object of interest in the X-ray image remains within the ultrasound plane, also the object of interest itself remains within the ultrasound imaging plane, since the object of interest naturally is situated on the line between the X-ray source and the projection of the object of interest. Indeed, the ultrasound plane is determined by the object of interest itself as well as the X-ray source, however with the object of interest being visualized by its projection on the X-ray detector. Thereby, it is ensured that the object of interest is also present in the ultrasound imaging plane. Inaccuracies in the imaging system, e.g. due to X-ray/ultrasound data registration errors or inaccuracies in the object of interest localization in the X-ray image, may require to tune the ultrasound slice thickness accordingly. Regularly, a slice thickness of 1, 2 or 3 mm is employed.

According to the present invention, a first ultrasound image plane is thus determinable by employing three points in space, i.e. the ultrasound transducer tip, the X-ray source as well as the projection of the object of interest on the X-ray detector. Using said information, a further, second ultrasound image plane may be set up, which contains the vector or line between the ultrasound transducer and the object of interest itself in 3D space within the reference coordinate system, which position itself is known from the first ultrasound image information under particular consideration of the registration between the ultrasound image data and the X-ray image data. Consequently, a second two-dimensional ultrasound image may be acquired containing said vector between the transducer tip and the object of interest, leaving a further degree of freedom, which can be arbitrarily adjusted. In other words, a second two-dimensional ultrasound plane may be turned about the line or vector between the transducer tip and the object of interest located within patient tissue. Often, such a second two-dimensional ultrasound plane can be placed orthogonally to the first ultrasound image plane, thereby acquiring at least some three-dimensional information, while still only using (two) two-dimensional images.

Put another way, assuming that the object of interest is also tracked in the first ultrasound plane, the second ultrasound image plane may be placed so that it passes through the object of interest. This leaves an extra degree of freedom for the interventionist to choose the orientation of the second ultrasound image plane freely, while still showing the object of interest. The tracking in the first ultrasound plane is greatly helped by the fact that the object of interest position is already known in the X-ray image and therefore the object of interest is constrained to lie on the corresponding epipolar line in the ultrasound image.

Now referring to FIG. 1, an exemplary embodiment of the relationship between ultrasound image information and X-ray image information according to the present invention is depicted.

In FIG. 1, a schematic of an imaging system employing both X-ray image acquisition as well as ultrasound image acquisition is depicted. An X-ray source 30 generates X-radiation 31, which is exemplarily embodied as a cone-beam directed towards an X-ray detector 32. X-ray detector 32 is exemplarily embodied as a two-dimensional X-ray detector, comprising a plurality of individual detector pixel elements arranged in a pixel array, which however is not depicted in detail in FIG. 1. In the path of X-radiation 31, an object of interest 36, the tool tip of a transcatheter tool, is depicted. The object of interest 36 generates a projection 38 on the two-dimensional X-ray detector 32. Accordingly, a vector or line 48 between the X-ray source 30 and the projection 38 of the object of interest 36 on X-ray detector 32 is established, on which line 48 also the object of interest 36 is required to be arranged.

Further, an ultrasound imaging apparatus embodied exemplarily as an ultrasound transducer 34 is shown in FIG. 1. Ultrasound transducer 34 is generating an ultrasound transmission 35, here directed towards the object of interest 36. A first line or vector 42a from the ultrasound transducer 34 to the X-ray source 30 as well as a second vector or line 42b from the ultrasound transducer 34 to the projection 38 of the object of interest 36 is depicted in FIG. 1. The first ultrasound plane 42 is thus established by the points in space of the ultrasound transducer 34, the X-ray source 30 and the projection 38 of the object of interest 36. Put another way, the ultrasound plane is established by paths or vectors 42a,b, and 48.

Establishing the first ultrasound plane 42 requires a known spatial relationship between the X-ray image information and the ultrasound image information, which may be performed by a registration operation of the C-arm acquisition geometry information and the ultrasound image information for obtaining a spatial relationship between said two image information. Known image processing techniques or further means like electromagnetic tracking using EM tracker elements may be employed for said registering operation. With said first ultrasound plane 42, also a location in space of the object of interest 36 is known. Subsequently, for a second ultrasound plane 44, this known location of the object of interest 36 together with the location of the ultrasound transducer 34 establishes a line or vector 50 between the ultrasound transducer 34 and the object of interest 36. The second ultrasound plane 44 thus comprises always the object of interest 36 by assuming that said second ultrasound plane 44 always comprises line 50, thereby allowing a degree of freedom 46, which can be chosen arbitrarily, e.g. by an operator of the imaging system 54. In other words, a further ultrasound image plane 44 may be turned about line 50 between the ultrasound transducer 34 and the object of interest 36. One preferred alignment of the first ultrasound plane 42 and the second ultrasound plane 44 is arranging both planes perpendicular to each another to establish some three-dimensional reference frame for an interventionist.

Figure 2:
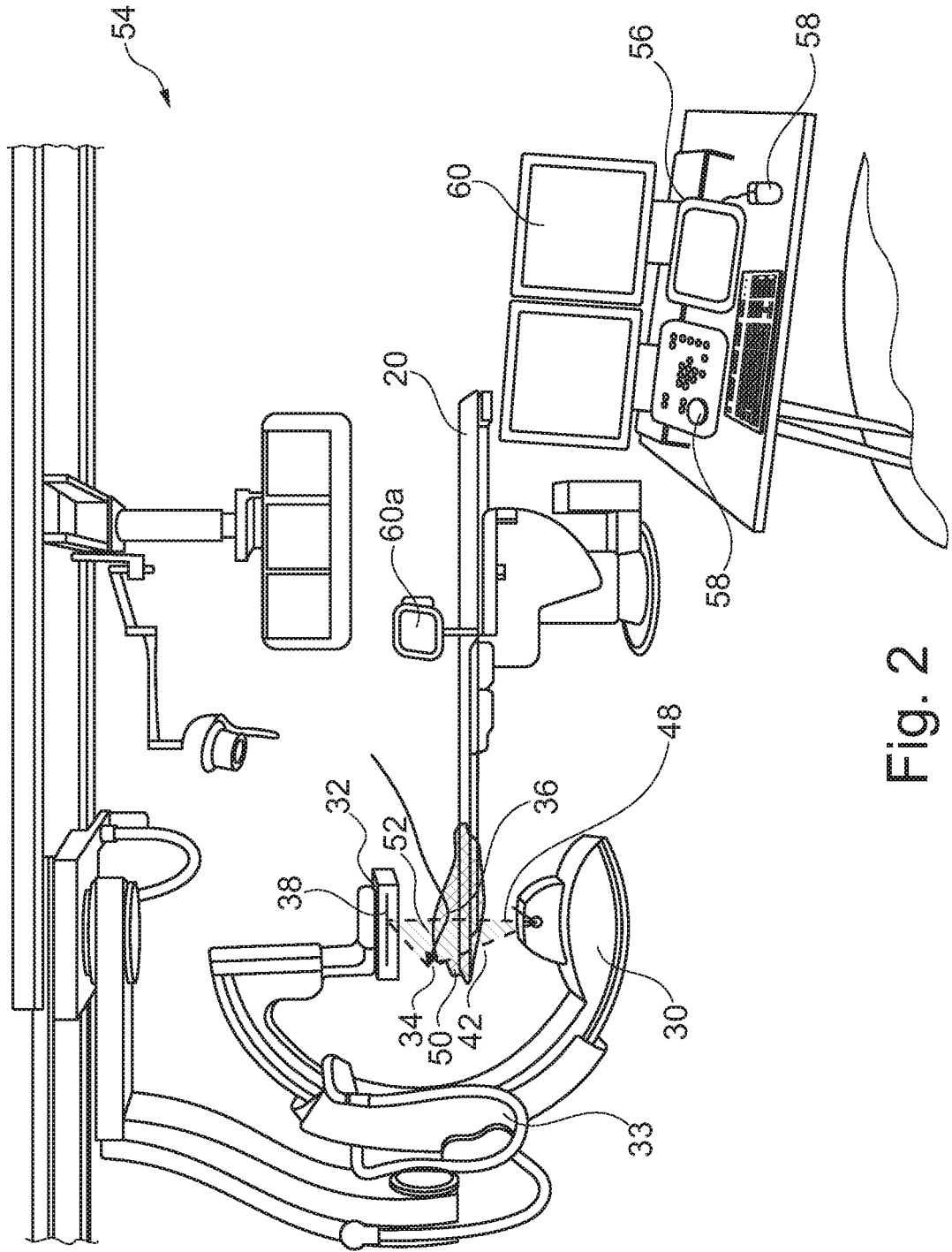
FIG. 2 shows an exemplary embodiment of a system for ultrasound image acquisition according to the present invention.

Now referring to FIG. 2, an exemplary embodiment of a system for ultrasound image acquisition according to the present invention is depicted.

An exemplarily application scenario employs a C-arc 33 comprising an X-ray source 30 as well as an X-ray detector 32 with X-radiation 31 being generated by the X-ray source 30 and being directed towards the X-ray detector 32. An object to be examined 52 is arranged in the path of X-radiation 31, which is subject to a transcatheter procedure with an object of interest 36, e.g. a transcatheter tool being inserted appropriately into object 52. An ultrasound transducer 34 is arranged in the vicinity of the object to be examined 52, in particular in the esophagus, embodied as a TEE ultrasound source. Said particular embodiment however is not depicted in FIG. 2, which is rather referring to a general ultrasound transducer 34.

A first ultrasound plane 42 is established by the X-ray source 30, the projection 38 of the object of interest 36 and the ultrasound transducer 34 in three-dimensional space.

Imaging system 54 comprises a processing element 56 with control elements 58, exemplarily embodied as keyboard and manual input devices, as well as a display unit 60 for displaying at least some image information of the X-ray image information and the first and second ultrasound image information. The operator of the imaging system 54 may provide a suitable image information on display 60a to the interventionist operating to assist in the procedure. By determining the three-dimensional position in space of the object of interest 36, a line 50 between the transducer 34 and the object of interest 36 may be established, allowing a second ultrasound plane 44, not depicted in FIG. 2 to be established, which may be turned about line 50 at the discretion of one of the operator and the interventionist.

Figure 3:
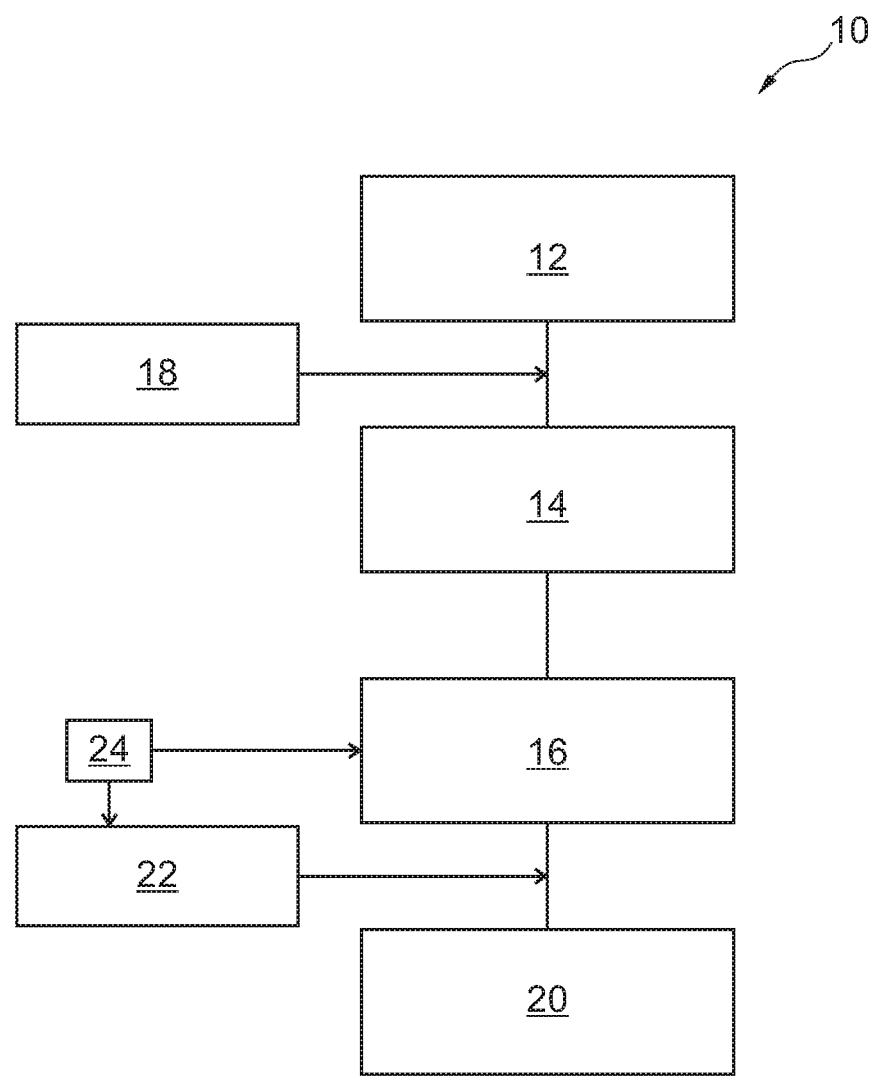
FIG. 3 shows an exemplary embodiment of a method for ultrasound image acquisition according to the present invention.

Now referring to FIG. 3, an exemplary embodiment of a method for ultrasound image acquisition according to the present invention is depicted.

FIG. 3 describes a method 10 for ultrasound image acquisition, in particular for tracking an object of interest in ultrasound image information comprising receiving 12 X-ray image information and ultrasound image information, detecting 14 an object of interest in the X-ray image information and steering 16 two-dimensional ultrasound image acquisition such that the object of interest is within the first ultrasound image plane. A registering procedure 18 aids in obtaining a spatial relation between the X-ray image information and the ultrasound image information. The determined first ultrasound image plane may be visualized 20. A second ultrasound image information corresponding to a second ultrasound image plane may be obtainable 22, which may also be visualized separately or conjointly with at least one of the first ultrasound image plane and the X-ray image information. An operator may adjust 24 the thickness of at least one of the first ultrasound image plane and the second ultrasound image plane to aid in having the object of interest within at least one of the respective image planes.

Another embodiment includes a computer-readable medium, in which a computer program for ultrasound image acquisition, in particular for tracking an object of interest in ultrasound image information is stored, which computer program, when being executed by a processing element, is adapted to carry out the method 10 for ultrasound image acquisition.

Yet another embodiment includes a program element for ultrasound image acquisition, in particular for tracking an object of interest in ultrasound image information, which program element, when being executed by a processing element, is adapted to carry out the method 10 for ultrasound image acquisition.

LIST OF REFERENCE SIGNS 10 method for ultrasound image acquisition
12 receiving X-ray image information and ultrasound image information
14 detecting an object of interest in the X-ray image information
16 steering two-dimensional ultrasound image acquisition
18 registering X-ray image information and ultrasound image information
20 visualizing 22 obtaining second ultrasound image information
24 adjusting slice thickness of ultrasound image plane
30 X-ray source
31 X-radiation
32 X-ray detector
33 C-arc
34 ultrasound transducer
35 ultrasound transmission
36 object of interest
38 projection
40 X-ray image information
42 first ultrasound image plane
44 second ultrasound image plane
46 degree of freedom
48 line X-ray source—projection object of interest
50 line ultrasound transducer—object of interest
52 object to be examined
54 imaging system
56 processing element
58 control element
60 display unit

The invention claimed is:

1. A system for ultrasound image acquisition and for tracking an object of interest in ultrasound image information comprising:
   an X-ray system having an X-ray source and an X-ray detector;
   an ultrasound system having a two-dimensional ultrasound image acquisition device including an ultrasound source; and
   a processor configured to:
      receive X-ray image information and ultrasound image information;
      detect an object of interest in the X-ray image information;
      register the X-ray image information and the ultrasound image information to determine a spatial relationship between the X-ray image information and the ultrasound image information;
      establish a first ultrasound image acquisition plane of the two-dimensional ultrasound image acquisition device defined by (i) a point in space of the ultrasound source, (ii) a point in space of the X-ray source, and (iii) a point in space of a projection of the object of interest on the X-ray detector; and
      steer the first ultrasound image acquisition plane of the two-dimensional ultrasound image acquisition device such that the object of interest, the X-ray source, the ultrasound source, and the projection of the object of interest on the X-ray detector are maintained within the first ultrasound image acquisition plane.

2. The system of claim 1, further comprising:
   a processing element;
   a control element; and
   a display unit.

3. The system of claim 1, wherein the processor is further configured to cause visualization of the two-dimensional ultrasound image information of the first ultrasound image acquisition plane.

4. The system of claim 1, wherein the ultrasound source is a TEE ultrasound source, and the object of interest is an interventional device.

5. The system of claim 1, wherein the processor is further configured to cause obtaining second ultrasound image information corresponding to a second ultrasound image acquisition plane comprising the ultrasound source and the object of interest defining a line in between such that a degree of freedom is available for orienting the second ultrasound image acquisition plane about the line.

6. The system of claim 1, wherein the processor is further configured to cause adjustment of the thickness of at least one of the first ultrasound image acquisition plane and the second ultrasound image acquisition plane to aid in having the object of interest within at least one of the respective image acquisition planes.

7. The system of claim 1, wherein the established first ultrasound image acquisition plane is defined by connecting (a) a first vector established between the ultrasound source and the X-ray source, (b) a second vector established between the ultrasound source and the projection of the object of interest on the X-ray detector, and (c) a third vector established between the X-ray source and the projection of the object of interest on the X-ray detector.

8. A method for ultrasound image acquisition and tracking an object of interest in ultrasound image information, comprising:
   receiving X-ray image information and the ultrasound image information;
   detecting an object of interest in the X-ray image information;
   registering the X-ray image information and the ultrasound image information to determine a spatial relationship between the X-ray image information and the ultrasound image information;
   establishing a first ultrasound image acquisition plane of a two-dimensional ultrasound image acquisition device defined by (i) a point in space of an ultrasound source, (ii) a point in space of an X-ray source, and (iii) a point in space of a projection of the object of interest on an X-ray detector;
   steering the first ultrasound image acquisition plane of the two-dimensional ultrasound image acquisition device such that the object of interest, the X-ray source, the ultrasound source and the projection of the object of interest on the X-ray detector are maintained within the first ultrasound image acquisition plane; and
   acquiring a two-dimensional ultrasound image along the first ultrasound image acquisition plane that includes the object of interest, the X-ray source, the ultrasound source, and the projection of the object of interest on the X-ray detector.

9. The method of claim 8, further comprising:
   visualizing the two-dimensional ultrasound image information of the first ultrasound image acquisition plane.

10. The method of claim 8, wherein the ultrasound source is a TEE ultrasound source, and wherein the object of interest is an interventional device.

11. The method of claim 8, further comprising:
    obtaining second ultrasound image information corresponding to a second ultrasound image acquisition plane comprising the ultrasound source and the object of interest defining a line in between such that a degree of freedom is available for orienting the second ultrasound image acquisition plane about the line.

12. The method of claim 8, further comprising:
    adjusting a thickness of at least one of the first ultrasound image acquisition plane and the second ultrasound image acquisition plane to aid in having the object of interest within at least one of the respective image acquisition planes.

13. The method of claim 8, wherein the established first ultrasound image acquisition plane is defined by connecting (a) a first vector established between the ultrasound source and the X-ray source, (b) a second vector established between the ultrasound source and the projection of the object of interest on the X-ray detector, and (c) a third vector established between the X-ray source and the projection of the object of interest on the X-ray detector.

14. A non-transitory computer readable medium comprising computer instructions for ultrasound image acquisition and tracking an object of interest in ultrasound image information which, when executed by a processor, cause the processor to:

receive X-ray image information and the ultrasound image information;

detect an object of interest in the X-ray image information;

register the X-ray image information and the ultrasound image information to determine a spatial relationship between the X-ray image information and the ultrasound image information;

establish a first ultrasound image acquisition plane of a two-dimensional ultrasound image acquisition device defined by (i) a point in space of an ultrasound source, (ii) a point in space of an X-ray source, and (iii) a point in space of a projection of the object of interest on a X-ray detector;

steer the first ultrasound image acquisition plane of the two-dimensional ultrasound image acquisition device such that the object of interest, the X-ray source, the ultrasound source,_ and the projection of the object of interest on a X-ray detector are maintained within the first ultrasound image acquisition plane; and acquire a two-dimensional ultrasound image along the first ultrasound image acquisition plane that includes the object of interest, the X-ray source, the ultrasound source and the projection of the object of interest on a X-ray detector.

15. The non-transitory computer readable medium of claim 14, wherein the established first ultrasound image acquisition plane is defined by connecting (a) a first vector established between the ultrasound source and the X-ray source, (b) a second vector established between the ultrasound source and the projection of the object of interest on the X-ray detector, and (c) a third vector established between the X-ray source and the projection of the object of interest on the X-ray detector.

* * * * *